United States Patent [19]

Sparks et al.

[11] Patent Number: 5,357,335
[45] Date of Patent: Oct. 18, 1994

[54] OPTICAL DETECTION DEVICE FOR SCREENING MAGNETIC TAPE

[75] Inventors: Johnny K. Sparks, White Bear Lake; Roger J. Anderson, St. Paul; Michael K. Hoel, Woodbury, all of Minn.

[73] Assignee: Minnesota Mining and Manufacturing Company, St. Paul, Minn.

[21] Appl. No.: 40,527

[22] Filed: Mar. 31, 1993

[51] Int. Cl.$^5$ ............................................. G01N 21/89
[52] U.S. Cl. .................... 356/237; 356/430; 356/445; 356/446
[58] Field of Search ............... 356/430, 431, 237, 445, 356/446

[56] References Cited

U.S. PATENT DOCUMENTS

| | | | |
|---|---|---|---|
| 4,395,127 | 7/1983 | Duvall | 356/430 |
| 4,408,884 | 10/1983 | Kleinknecht et al. | 356/237 |
| 4,682,040 | 7/1987 | Hohki et al. | 356/445 |
| 4,789,238 | 12/1988 | Ichikawa et al. | 356/237 |
| 4,988,204 | 1/1991 | Sakaguchi et al. | 356/430 |
| 5,000,569 | 3/1991 | Nylund | 356/237 |
| 5,096,299 | 3/1992 | Shizuya | 356/446 |
| 5,249,034 | 9/1993 | Minato | 356/237 |
| 5,274,434 | 12/1993 | Morioka et al. | 356/237 |
| 5,278,635 | 1/1994 | Ono et al. | 356/446 |

FOREIGN PATENT DOCUMENTS 60-211954 10/1985 Japan ................................ 356/237
62-42039 2/1987 Japan ................................ 356/237

OTHER PUBLICATIONS

Technical Datasheet from Silicon Detector Corporation, 5 pages, Sep. 1977, "General Purpose Detectors".
"GaAlAs Hermetic Infrared Emitting Diodes" from Optek Product Bulletin OP231W, Jul. 1989.

Primary Examiner—Rolf Hille
Assistant Examiner—Minhloan Tran
Attorney, Agent, or Firm—Gary L. Griswold; Walter N. Kirn; Eric D. Levinson

[57] ABSTRACT

An optical detection device for screening magnetic tape for physical defects. The device has three light emitting diodes in a row perpendicular to the direction of travel of the tape. Two rows of photovoltaic detectors having three and two detectors, respectively, are parallel to the row of diodes. The diodes direct light toward the surface of the tape. If no physical defects are present, the light is reflected at the tape surface to the detectors. If a physical defect is present, the light is scattered by the defect and the amount of light which reaches the detector is reduced.

15 Claims, 2 Drawing Sheets

OPTICAL DETECTION DEVICE FOR SCREENING MAGNETIC TAPE

FIELD OF THE INVENTION

The invention relates generally to optical detection systems used to screen magnetic tape for physical defects and more specifically to the optical detection devices employed by such systems.

BACKGROUND OF THE INVENTION

Magnetic recorders can read and write information on magnetic tape. The presence of physical defects on the surface of the tape can cause the recorder to misread the information on the tape, resulting in a reading "error". Such physical defects typically include scratches on the surface of the tape, crinkles in the tape itself, or the presence of large particles on the tape.

It is known that optical detection devices can be used to detect physical defects in magnetic tape. Such devices can be located on the same side of the tape as a light source so as to detect light that is reflected at the surface of the tape. In the alternative, the detection device can be located on the opposite side of the tape from the light source so as to detect light which passes through the tape. In either case, light which contacts a flat portion of the tape surface will be reflected/transmitted toward detectors in the detection device. Light which strikes a physical defect on the surface of the tape will be scattered and thus will not be detected by the detectors. Whenever one of the detectors fails to receive enough light, an indicator light is lit to indicate that the tape is defective.

Detection devices employing various light source and detector arrays have been used to detect physical defects on the surface of magnetic tape. One array includes a single row of detectors spanning the width of the tape. Another array uses approximately 24 detectors in a two-dimensional array where the detectors are aligned in several columns which are not quite parallel with the direction of travel of the tape. Another method of detecting tape surface defects is to utilize a row or array of fiber optic strands to receive the light and convey it to the detectors.

The optical detection device must be able to detect all physical defects of a certain size, regardless of their location on the tape. If too few detectors are used, there is the risk that physical defects on the tape may be missed. The use of too many detectors, however, needlessly increases the cost of the device.

It would be desirable to have an optical detection device for screening for defects in magnetic tape which uses a minimum number of detectors and yet can reliably detect all physical defects of a particular size regardless of their location on the tape surface.

SUMMARY OF THE INVENTION

The invention provides an optical detection device having a simplified design for reliably detecting physical defects on magnetic tape. The device has a row of at least two, and preferably three, light-emitting diodes which are configured to direct light toward the magnetic tape to be screened. The row of diodes extends across the width of the tape and is substantially perpendicular to the direction of travel of the tape. The device also has two rows of at least two detectors which are parallel to the rows of diodes. The two rows are configured to receive light from the diodes which has been reflected from a surface of the tape having no defects. The row of detectors closest to the row of diodes preferably has three detectors; the other row preferably has two.

The device can include a pair of mirrors, one positioned at each end of the row of detectors closest to the diodes, so that the light emitted from the diodes toward each edge of the tape will be reflected at the tape surface toward each mirror, where it is reflected toward the detectors at each end of the row of detectors.

The invention also includes a method of detecting physical defects in a magnetic tape. The method includes passing a magnetic tape past the optical detection device described above. The light received by the detectors is then converted into electrical signals. The signals are then analyzed to determine whether a defect is present. The method is particularly useful for screening digital data recording tape for defects greater than about 1 mm in size.

The invention also includes an optical detection system for accomplishing the method described above.

BRIEF DESCRIPTION OF THE DRAWINGS

The invention will now be described by referring to the following Figures, in which.

DETAILED DESCRIPTION

Figure 1:
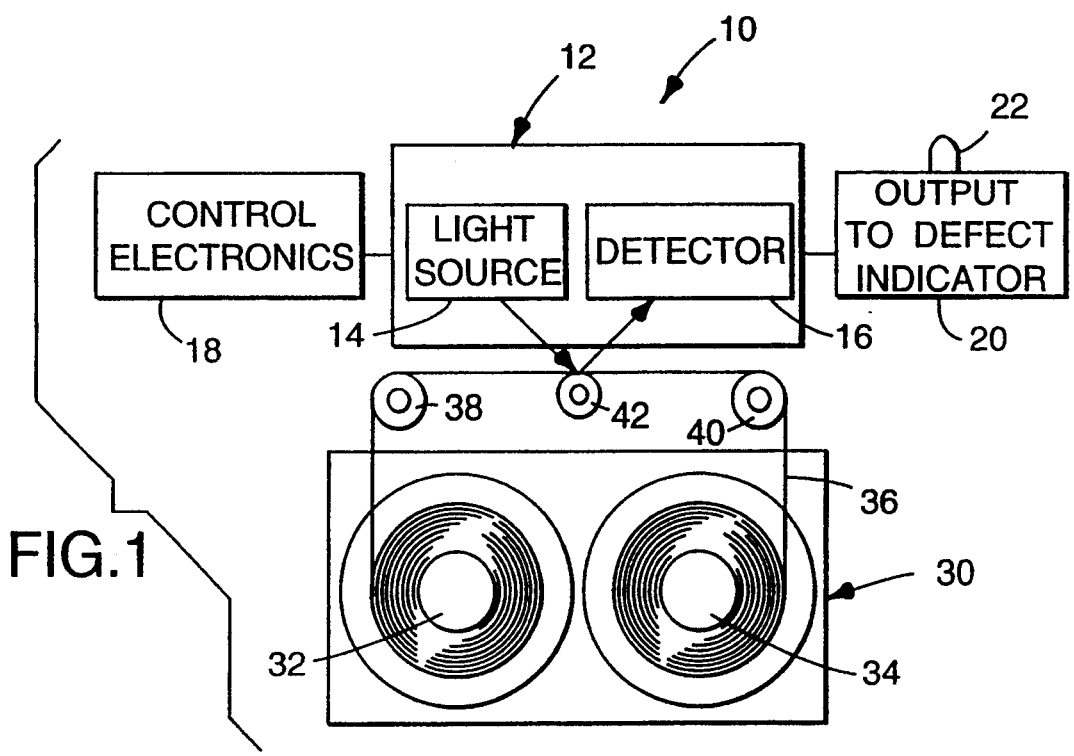
FIG. 1 is a schematic diagram of an optical detection system according to the invention.

A schematic diagram of an optical detection system 10 according to the invention is shown in FIG. 1. The system 10 is comprised of an optical detection device 12, control electronics 18, output 20, indicator light 22, tape guide rollers 38 and 40, and a backer 42. The system 10 includes an array of light sources 14 and an array of detectors 16. A cassette cartridge 30 has hubs 32 and 34 upon which magnetic tape 36 is wound.

Screener 10 can be used to optically screen tape 36 for physical defects on the surface of the tape by moving the tape past optical detection device 12 along a path provided by guide rollers 38 and 40. Detection device 12 is then moved into position next to tape 36 at a point between guide rollers 38 and 40. Backer 42 is provided against the side of tape 36 opposite device 12 to prevent the tape from fluttering toward and away from the device.

Light from light source array 14 is directed toward the surface of tape 36. In the absence of any physical defects on the surface of the tape 36, the light will be reflected toward and sensed by detector array 16. If physical defects are present, however, the light from light source array 14 will not be properly reflected at the surface of the tape, thereby reducing the amount of light that reaches detector array 16. This reduction in the amount of light sensed by detector array 16 is analyzed by control electronics 18. If the reduction of light is complete or long enough, control electronics 18 signals to output 20 to light indicator light 22, which signals the operator that cartridge 30 contains defective tape 36. At that point, the defective portion of tape 36 can be repaired or removed, or the entire cartridge can be discarded.

Control electronics 18 can be adjusted to allow optical detection system 10 to detect physical defects of various sizes. This can be done by passing a tape or tapes having physical defects of known size past detection device 12. Optical detection system 10 is preferably calibrated to detect only physical defects which are at least 0.5 mm in size. More preferably, system 10 is calibrated to detect only physical defects which are larger than about 1 mm in size.

Optical detection system 10 can also be used to screen tape 36 before it is installed in a cartridge. In that case, hubs 32 and 34 would represent large reels capable of holding a large quantity of tape 36. Tape 36 can be any kind of magnetic recording tape, but it is preferably digital data recording tape, which typically has a width of from about 4 mm to 51 mm.

Figure 2:
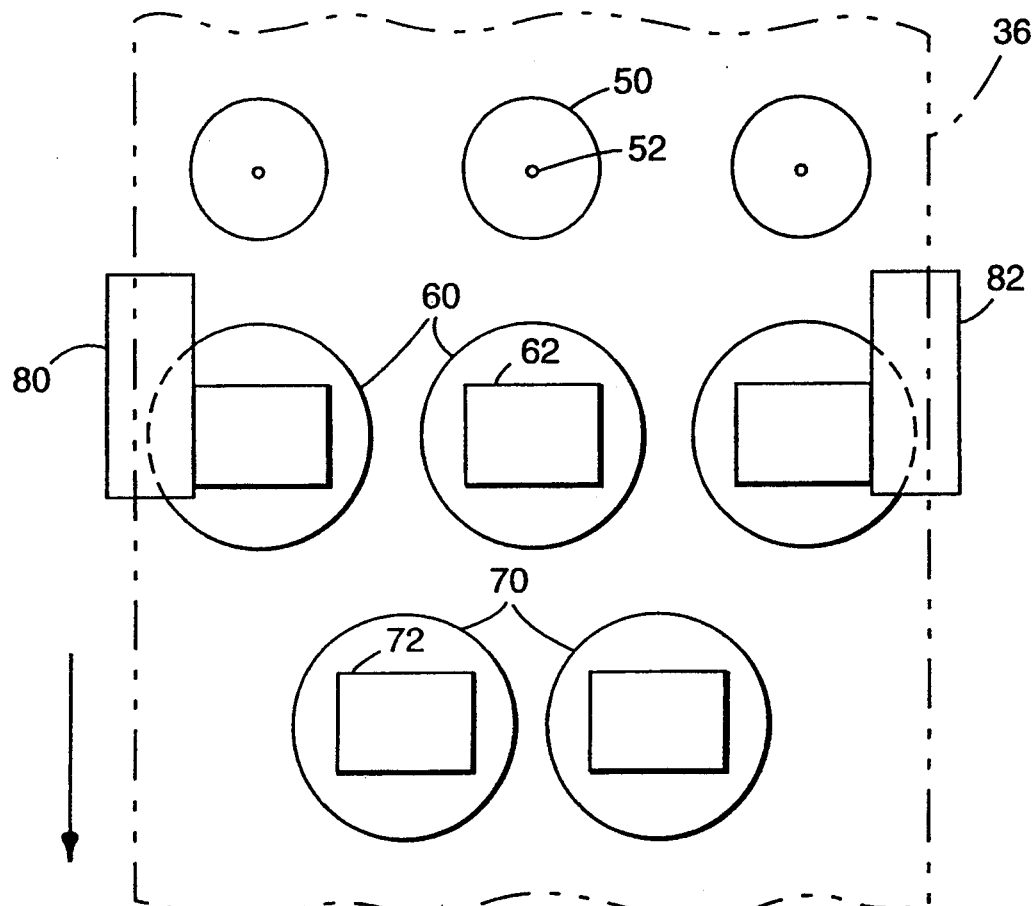
FIG. 2 is a schematic diagram showing an optical detection device according to the invention.

A schematic diagram showing the arrangement of light source array 14 and detector array 16 in detection device 12 is shown in FIG. 2. Light source array 14 includes at least two, and preferably three, light emitting diodes 50 which emit light from point sources 52 in the center of the diode. Diodes 50 are aligned in a row across the width of tape 36 to be screened. The row of diodes 50 is substantially perpendicular to the direction of travel of tape 36 past the diodes. Diodes 50 are preferably spaced as shown in FIG. 2.

Detector array 16 includes a first, or front, row of detectors 60 and a second, or back, row of detectors 70. Each row of detectors 60 and 70 preferably has at least two detectors. More preferably, the first row has three detectors 60 and the back row has two detectors 70, as shown in FIG. 2. Detectors 60 and 70 have effective sensing areas 62 and 72, respectively. Each row of detectors 60 and 70 spans the width of tape 36 and is substantially parallel to the row of diodes 50. Detectors 60 and 70 are preferably spaced as shown in FIG. 2.

The number of front detectors 60 should match the number of diodes 50. The number of back detectors 70 is preferably one less than the number of front detectors 60, and the back detectors should be spaced so that they would fill the gaps between adjacent front detectors if the back detectors were pushed up to the row of front detectors.

Mirrors 80 and 82 are positioned at each end of the first row of detectors 60. Mirrors 80 and 82 are preferably elongated with their long axes extending parallel with the length of tape 36 and in the same plane as the tape. The short axes of mirrors 80 and 82 are preferably oriented at an angle of 11° with respect to the plane of tape 36 in the direction of detectors 60, so that the bottom half of each mirror is even with the tape surface.

Light emitted from diodes 50 toward each edge of tape 36 is reflected at the tape surface toward mirrors 80 and 82 which reflect the light back to detectors 60 at each end of the row of front detectors 60. This allows detection device 12 to sense physical defects at the edge of tape 36. If there is a large enough defect at an edge of tape 36, light reflected at the defect will not be properly reflected toward front detectors 60 and the detectors will sense the reduction in light, and thus, the defect.

Figure 3:
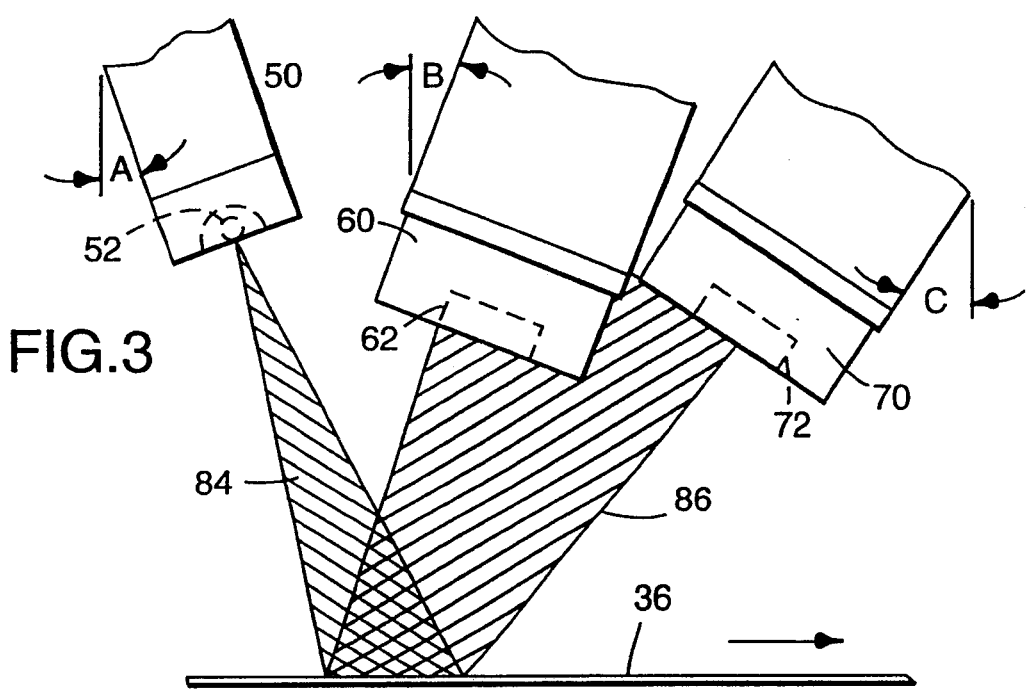
FIG. 3 is a side schematic view of the device of FIG. 2.

A side diagrammatical view of diodes 50 and detectors 60 and 70 is shown in FIG. 3. Diodes 50 are oriented at an angle A with respect to the direction of the normal to the surface of tape 36. The angle A is preferably within the range of from about 10° to 30°, more preferably from 15° to 25°, and most preferably is about 20°. Point sources 52 in diodes 50 emit light beam 84 which increases in cross-sectional area as its distance from the diode increases. Cone-shaped light beam 84 preferably widens at an angle of about 20°. Thus, if angle A is about 20°, light rays in light beam 84 will strike tape 36 at angles ranging from about 10° to 30°.

Front detectors 60 are oriented at an angle B with respect to the surface normal of tape 36. Angle B is preferably approximately equal and opposite to angle A, e.g., 20°, thereby allowing front detectors 60 to receive most of reflected beam 86 from light beam 84.

Back detectors 70 are oriented at an angle C to the surface normal of tape 36. Angle C is preferably greater than angle B so that light rays in reflected beam 86 which do not strike front detectors 60 reach back detectors 70. Angle C is preferably within the range of from about 20° to 40°, more preferably 25° to 35°, and most preferably 30°. Back detectors 70 are oriented to receive light rays at the edge of light beam 84 closest to detectors 60. If angle A is 20°, and the cone of light beam 84 is 20° wide, i.e., 10° on either side of the center light ray, then some light rays will strike the surface of tape 36 at an angle of 30°. These light rays will be detected by back detectors 70 if they are oriented at an angle of about 30°.

Figure 4:
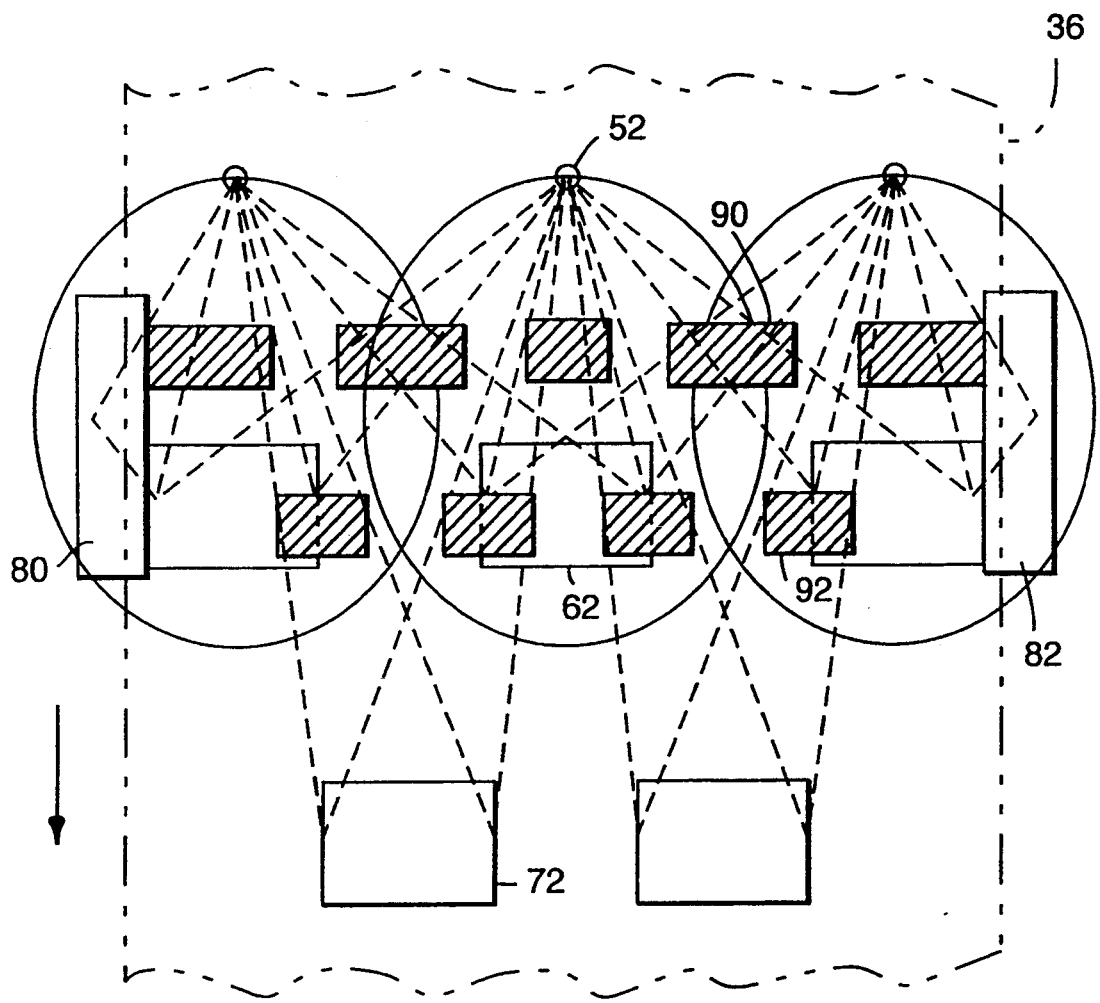
FIG. 4 is a ray diagram showing the areas of coverage of the device of FIG. 2.

A ray diagram showing the approximate coverage of detectors 60 and 70 is shown in FIG. 4. A first row of defect areas 90 spans the width of tape 36. A second row of defect areas 92 also spans the width of tape 36, but defect areas 92 are positioned to fill in the gaps of the row of defect areas 90 if the two rows were pushed together. Defect areas 90 and 92 represent areas in which a defect could be present, not the actual size of a defect. Detection device 12 will be able to sense any defect across the entire width of the tape because detectors 60 and 70 are able to cover all of defect areas 90 and 92.

As can be seen from the ray diagram in FIG. 4, each defect area 90 and 92 is covered by at least one detector 60 or 70. Furthermore, even the edges of tape 36 are covered due to mirrors 80 and 82.

Diodes 50 preferably emit infrared light, that is light having a wavelength greater than 650 nm. Diodes 50 preferably have a half-power point of 20°. One such diode is a gallium aluminum arsenide (GaAlAs) hermetic infrared emitting diode, such as types OP232W and OP233W from Optek Technology, Inc., Carrollton, Tex., which emits infrared light having a wavelength of 890 nm.

Detectors 60 and 70 are preferably photovoltaic detectors. One such detector is available from Silicon Detector Corporation in Camarillo, Calif. as model number SD-172-11-11-021 (Isolated)-221.

The invention will now be illustrated by the following non-limiting example.

EXAMPLE

Seventeen digital data recording tapes having a width of 25.4 mm and having physical defects of at least 0.5 mm in size were screened by optical detection system 10, as shown in the Figures, which was calibrated to detect defects of that same size. The diodes and detectors used were from Optek Technology and Silicon Detector Corporation, respectively, as described above. The tapes were run past the optical detection device 12 at a speed of 1.5 m/s. The detection system correctly indicated that defects were present for 16 of the 17 tapes.

What is claimed is:

1. An optical detection device for screening magnetic tape for physical defects, including:

a row of at least two light emitting diodes, wherein the diodes are configured to direct light toward a magnetic tape to be screened, and wherein the row of diodes extends across the width of the tape and is substantially perpendicular to the direction of travel of the tape;

first and second rows, substantially parallel to the row of diodes, each of which includes at least two detectors, wherein the first row is positioned between the row of diodes and the second row, and wherein the detectors in both rows are configured to receive light from the diodes which has been reflected from a surface of the tape when physical defects on the tape are not present; and a pair of mirrors, wherein one mirror is positioned at each end of the first row of detectors, whereby light emitted from the diodes toward each edge of the tape is reflected at the tape surface toward each mirror, where it is reflected toward the detectors at each end of the first row when physical defects are not present.

2. The optical detection device of claim 1, wherein the row of diodes has three diodes, the first row of detectors has three detectors, and the second row of detectors has two detectors.

3. The optical detection device of claim 1, wherein the diodes emit light toward the tape surface at an average angle of about 20° with respect to the tape surface normal.

4. The optical detection device of claim 3, wherein the detectors in the first row are oriented at an average angle of about 20° with respect to the tape surface normal, and wherein the detectors in the second row are oriented at an angle of about 30° with respect to the tape surface normal.

5. The optical detection device of claim 1, wherein the detectors are photovoltaic detectors and the diodes emit light having a wavelength greater than about 650 nm.

6. A method of detecting physical defects on a magnetic tape, including:

passing a magnetic tape past a row of at least two light emitting diodes, wherein the row of diodes extends across the width of the tape and is perpendicular to the direction of travel of the tape;

emitting light from the diodes toward a surface of the tape to be analyzed, whereby the light is reflected at the surface;

detecting the reflected light with an array of detectors consisting essentially of first and second rows of detectors, wherein each row is parallel to the row of diodes and includes at least two detectors, and wherein a mirror is positioned at each end of the first row of detectors, whereby light emitted from the diodes toward each edge of the tape is reflected at the tape surface toward each mirror, where it is reflected toward the detectors at each end of the first row when physical defects are not present;

converting the reflected light detected by the detectors into electrical signals;

analyzing the signals to determine whether a physical defect is present; and indicating whether a physical defect is present.

7. The detection method of claim 6, wherein the magnetic tape is digital data recording tape.

8. The detection method of claim 6, wherein the row of diodes has three diodes, the first row of detectors has three detectors, and the second row of detectors has two detectors.

9. The detection method of claim 6, wherein the diodes emit light toward the tape surface at an average angle of about 20° with respect to the tape surface normal.

10. The detection method of claim 9, wherein the detectors in the first row are oriented at an average angle of about 20° with respect to the tape surface normal, and wherein the detectors in the second row are oriented at an angle of about 30° with respect to the tape surface normal.

11. The detection method of claim 6, wherein the detectors are photovoltaic detectors and the diodes emit light having a wavelength greater than about 650 nm.

12. The detection method of claim 6, wherein the method only detects defects on the tape which are at least 0.5 mm in size.

13. The detection method of claim 6, wherein the method only detects defects on the tape which are at least 1 mm in size.

14. An optical detection system for screening magnetic tape for physical defects, including:

an optical detection device including:

a row of at least two light emitting diodes, wherein the diodes are configured to direct light toward a magnetic tape to be screened, and wherein the row of diodes extends across the width of the tape and is substantially perpendicular to the direction of travel of the tape;

first and second rows, substantially parallel to the row of diodes, each of which includes at least two detectors, wherein the first row is positioned between the row of diodes and the second row, and wherein the detectors in both rows are configured to receive light from the diodes which has been reflected from a surface of the tape when physical defects on the tape are not present; and a pair of mirrors, wherein a mirror is positioned at each end of the first row of detectors, whereby light emitted from the diodes toward each edge of the tape is reflected at the tape surface toward each mirror, where it is reflected toward the detectors at each end of the first row when physical defects are not present;

means for passing a magnetic tape past the detection device;

means for analyzing signals from the detectors to determine whether a physical defect is present; and means for indicating the presence of the defect.

15. The optical detection system of claim 14, wherein the row of diodes has three diodes, the first row of detectors has three detectors, and the second row of detectors has two detectors.

* * * * *